United States Patent [19]

Roeske

[11] Patent Number: 4,851,385

[45] Date of Patent: Jul. 25, 1989

[54] LHRH ANTAGONIST ANALOGS HAVING LOW HISTAMINE-RELEASE ACTIVITY

[75] Inventor: Roger W. Roeske, Indianapolis, Ind.

[73] Assignee: Indiana University Foundation, Bloomington, Ind.

[21] Appl. No.: 73,929

[22] Filed: Jul. 15, 1987

[51] Int. Cl.4 .................... A61K 37/43; C07K 7/20
[52] U.S. Cl. ................................. 514/15; 514/800; 530/313
[58] Field of Search ................. 530/313; 514/15, 800

[56] References Cited

U.S. PATENT DOCUMENTS

| | | | |
|---|---|---|---|
| 4,317,815 | 3/1982 | Coy et al. | 530/313 |
| 4,431,635 | 2/1984 | Coy et al. | 530/313 |
| 4,481,190 | 11/1984 | Nestor et al. | 530/313 |
| 4,504,414 | 3/1985 | Folkers et al. | 530/313 |
| 4,652,550 | 3/1987 | Rivier et al. | 530/313 |
| 4,689,396 | 8/1987 | Roeske et al. | 530/313 |
| 4,740,500 | 4/1988 | Vale, Jr. et al. | 530/313 |

*Primary Examiner*—Delbert R. Phillips
*Attorney, Agent, or Firm*—Kirkland & Ellis

[57] ABSTRACT

Antagonist analogs of luteinizing hormone-releasing hormone (LHRH) having N-alkylated basic amino acid residues at the 8 position, 8 and 6 positions, 8 and 5 positions, and 8, 6 and 5 positions, having high antiovulatory activity and low histamine release activity, and their use in regulating the release of gonadatropic hormones from the pituitary gland of mammals.

19 Claims, No Drawings

LHRH ANTAGONIST ANALOGS HAVING LOW HISTAMINE-RELEASE ACTIVITY

BACKGROUND OF THE INVENTION

This invention was made with Government support under contract Nos. N01-HD-4-2834 and N01-HD-2-2808 awarded by the National Institutes of Health. The Government has certain rights in this invention.

This invention relates to peptides which inhibit the release of gonadatropins by the pituitary gland in mammals, including humans, and to methods of preventing ovulation and/or inhibiting the release of steriods in mammals.

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as luteinizing hormone-releasing hormone ("LHRH").

It has been isolated and characterized as a decapeptide having the following structure:

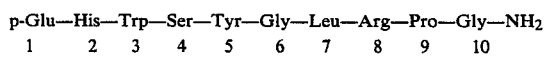

p-Glu—His—Trp—Ser—Tyr—Gly—Leu—Arg—Pro—Gly—NH$_2$
  1    2    3    4    5    6    7    8    9    10

Conventional abbreviations are used for the individual amino acids of this compound and throughout this disclosure as recommended by the IUPAC-IUB Commission on Biochemical Nomenclature, Biochemistry, 11 1726 (1972).

The administration of LHRH analogs that are antagonistic to the normal function of LHRH has been used to prevent ovulation and thus such antagonist analogs are useful as contraceptives. LHRH antagonist analogs have also been found useful to regulate the secretion of gonadatropins in male mammals and can be employed as male contraceptives. These analogs may also be used to inhibit the production of gonadatropins and sex hormones under various circumstances including precocious puberty, hormone dependent neoplasia, dysmenorrhea and endometriosis.

Antagonists function by competing with LHRH for the appropriate receptors and thus high doses are typically required to block out the natural peptide. Accordingly, much research has focussed on designing LHRH analogs having a high degree of potency and resistance to enzymatic degradation. See generally, Karten, M. J. and J. E. Rivier, Vol. 7, No. 1 Endocrine Reviews, 44 (1986); U.S. Pat. No. 4,481,190 to Nestor, and U.S. Pat. No. 4,547,370 to Roeske.

Many effective synthetic antagonist analogs of LHRH have pituitary receptor binding affinities of 10 to 20 times that of LHRH itself. Generally the best antagonists have a median effective dose of about one microgram per animal in the rat antiovulatory assay. Corbin, A. and Beattie, C. W., Endocrine Research Communications 2 1 (1975). Most of the potent LHRH antagonists have a D-amino acid substituted for histidine at the 2 position, a D-arginine residue in position 6, L-arginine in position 8, and a hydrophobic cluster of residues at the N-terminal part of the molecule, including N-acylation of the amino acid at position 1. For example, a typical high potency autiovulatory LHRH analog is [N-Ac-D-Nal(2)$^1$, D-p-Cl-Phe$^2$, D-Trp$^3$, D-Arg$^6$, D-Ala$^{10}$] LHRH, (compound (1) of Table I herein); where the superscript indicates the position of the amino acid residue within the peptide; all amino acid residues have the "L" configuration unless otherwise indicated; and the brackets followed by "LHRH" indicate that the unspecified positions within the brackets are occupied as in the native molecule LHRH. For example, in this analog the unspecified native amino acid residues are Ser$^4$, Tyr$^5$, Leu$^7$, Arg$^8$, and Pro$^9$.

In mammals these antagonists, especially those having D-arginine or D-Lysine substituted at the 6 position and a cluster of hydrophobic amino acids at the N-terminus, have been associated with histamine release and its attendant adverse side effects such as edema of the face and extremities and cutaneous anaphylactoid-like reaction in rats causing a dose-related whealing response. For example, Compound (1) of Table I has D-Arg at the 6 position and is a potent histamine releasing anlog. See Karten and Rivier, Vol. 7, No. 1, Endocrine Reviews, 44, 59 (1986) and publications cited therein. Although the histamine release activity of the analogs is not related to their potency as LHRH antagonists, such adverse side effects must be eliminated or greatly reduced, while maintaining high antiovulatory potency if the antagonists are to be useful.

Distancing the natural Arg at the eight position from the synthetic Arg at the 6 position is known to decrease the adverse histamine release activity of synthetic antagonist analogs. For example, [Ac-2-D-Nal$^1$, α-Me-4-Cl-D-Phe$^2$, D-Trp$^3$, Arg$^5$, D-Tyr$^6$, D-Ala$^{10}$] LHRH is approximately 20–40 times less potent than the synthetic D-Arg$^6$ antagonists in histamine releasing activity. Roeske, R. W., et. al., 1985 Proceedings of the Ninth American Peptide Symposium, Pierce Chemical Co., Rockford, Ill., at p. 561. Replacement of the arginine residue at the six position with D-pyridinium alanine ("D-Pal") is known to give antagonist having somewhat reduced, but nevertheless adverse, histamine release activity. Folkers, K. et. al, Biochem. Biophys. Res. Comm. 137 709 (1986). And in general, analogs having arginine at the five position and a D-hydrophobic residue at the six position are known to be only 3% to 5% as active in releasing histamine, but have lower antiovulatory potency than the corresponding analogs having native tyrosine at the five position and D-arginine at the six position.

It is a primary object of this invention to provide high potency antiovulatory antagonist LHRH analogs having low histamine release activity.

SUMMARY OF THE INVENTION

This invention overcomes the disadvantages of the prior art by providing novel antagonist analogs of LHRH where replacement of the amino acid residue at position 8 with an N-alkylated basic amino acid residue gives an LHRH analog having high antagonist antiovulatory potency but low histamine release activity. Further substitutions at the 5 or 6 positions with the N-alkylated basic amino acid residue also give LHRH antagonist analogs having high antiovulatory activity and low histamine releasing activity.

The analogs of the present invention have the formula:

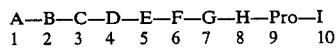
$$\begin{array}{cccccccccc} A & B & C & D & E & F & G & H & Pro & I \\ 1 & 2 & 3 & 4 & 5 & 6 & 7 & 8 & 9 & 10 \end{array}$$

and the pharmaceutically acceptable salts thereof wherein:

A: is an amino acyl residue selected from the group consisting of N-Ac-D,L-phenylalanyl, N-Ac-D,L-p-chlorophenylalanyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, and 3-(4-trifluoromethylphenyl)-D,L-alanyl;

B: is an amino acyl residue selected from the group consisting of D-phenylalanyl, D-p-Cl-phenylalanyl, D-p-F-phenylalanyl, 3-(3,4,5-trimethoxyphenyl)-D-alanyl, D-α-methyl-p-Cl-phenylalanyl and 3-(2,4,6-trimethylphenyl)-D-alanyl;

C: is an amino acyl residue selected from the group consisting of D-tryptophanyl, D-phenylalanyl, D-Me$^5$-phenylalanyl, 3-(3-pyridyl)-D-alanyl, 3-(1-naphthyl)-D-alanyl, and 3-(2-naphthyl)-D-alanyl;

D: is an amino acyl residue selected from the group consisting of L-seryl and L-ornithyl;

E: is an amino acyl residue selected from the group consisting of tyrosyl, Nε-isopropyl lysyl, isoleucyl, arginyl, lysyl and N-methyl 3-pyridinium alanyl;

F: is an amino acyl residue selected from the group consisting of D-arginyl, D-Nε-isopropyl lysyl, D-tyrosyl, D-N-methyl 3 pyridinium alanyl, D-tryptophanyl, and 3-2-naphthyl-D-alanyl;

G: is an amino acyl residue selected from the group consisting of leucyl, norleucyl, norvalyl and phenylalanyl;

H: is an amino acyl residue selected from the group consisting of arginyl, diethylhomoarginyl, Nε-isopropyl lysyl, Nε-trimethyl lysyl, and N-methyl-3-pyridinium alanine;

I: is a member selected from the group consisting of D-alaninamide, D-leucinamide, glycinamide; and —NHR wherein R is alkyl having from one to four carbon atoms, or NHCONH$_2$.

Preferred embodiments of the present invention are LHRH antagonist analogs where Nε-isopropyl lysine ("Lys(iPr)") and Nε-trimethyl lysine ("Lys(Me$_3$)") are substituted at the 8 position and at the 5 or 6 positions of the natural LHRH decapeptide.

Another preferred embodiment of the present invention is the D-Lys(iPr)$^6$, Lys(iPr)$^8$ substitution analog having a further substitution of N-methyl-3-pyridinium alanine ("Me-Pal") at position 5.

Another preferred embodiment is the Lys(iPr)$^{5,8}$ substitution analog having a further substitution of Me-Pal at position 6.

DETAILED DESCRIPTION OF THE INVENTION

Generally the low histamine releasing activity of the antiovulatory LHRH antagonist analogs of the present invention is achieved by substituting an N-alkylated basic amino acid residue for the arginine residue at the 8 position of the natural LHRH polypeptide. The low histamine release activity of the analogs of the present invention is enhanced, while maintaining high antiovulatory activity, by further substituting an N-alkylated residue at either the 5 or 6 positions for the tyrosine or glycine residues respectively of the natural LHRH polypeptide and preferably by making such N-alkylated basic amino acid residue substitutions at all three positions.

A common LHRH analog known to be a potent LHRH antagonist but also known to have high histamine releasing activity is [N-Ac-D-Nal(2)$^1$, D-pCl-Phe$^2$, D-Trp$^3$, D-Arg$^6$, D-Ala$^6$, D-Ala$^{10}$]LHRH, Compound (1) in Table I). This compound has been selected as a base for comparing the antiovulatory activity and histamine releasing activity of the compounds of the present invention. Compounds showing histamine release activity at effective mean doses of about three or more micrograms per milliliter in the histamine release assay described below are considered to have low histamine releasing activity. That is, a very high dose must be given before the adverse histamine response occurs. Compounds showing inhibition of ovulation at effective mean doses of one or less micrograms per rat in the antiovulatory assay described below are considered to have high antiovulatory potency. That is, a desirably small dose is required to inhibit ovulation.

The base compound (1) of Table I has histamine release activity at a mean effective dose as low as 0.10 ug/ml. The analogs of the present invention require mean effective doses of about 3.0 ug/ml or more for histamine release. The most effective analogs of the present invention, such as compounds (7), (9) and (12) in Table I have mean effective doses of about 9.0 ug/ml. Known analogs designed in an effort to lower histamine release activity, such as [N-Ac-D-Nal(2)$^1$, D-pCl-Phe$^2$, D-Pal$^3$, Arg$^5$, D-Tyr$^6$, D-Ala$^{10}$]LHRH have mean effective doses of about 4.0 ug/ml. See Roeske, R. W. et al. "Substitution of Arg$^5$ for Tyr$^5$ in GnRH antagonists" in Peptides: Structure and Foundation, Deber, C. M., et al. (Eds.), Pierce Chemical Co., Rockford, Ill., 1985, at page 561.

The N-alkylation of the residues at positions 5, 6 and 8 in the present invention should be limited to 6 or fewer carbon atoms. For example, N-alkylation of lysine residues in positions 6 and 8 with a 7-carbon moiety, such as: [Ac-D-2-Nal$^1$, D-4-Cl-Phe$^2$, D-Trp$^3$, D-Nε-Heptyl Lys, Nε-Heptyl Lys$^8$, D-Ala$^{10}$]LHRH, lowers antiovulatory activity markedly.

Analogs having especially low histamine releasing activity yet retaining potent antiovulatory activity have either a D-Me-Pal$^6$ or D-Lys(iPr)$^6$ with an Lys(iPr)$^8$ residue together with either an aliphatic residue (Ile) or a positively charged residue (Me-Pal or Lys(iPr)) in position 5. These are compounds (7), (12) and (11) of Table I having mean effective doses of 9.92, 7.9 and 9.72 ug/ml respectively in the histamine release assay.

As shown in Table I, although both the Lys(iPr)$^8$ and Lys(Me$_3$)$^8$ substitutions give analogs having low histamine release activity and high antiovulatory activity, a comparison of compounds (9) and 10) shows the Lys(iPr)$^8$ is the preferred substitution giving lower histamine release activity than the Lys(Me$_3$)$^8$ substitution. Even better results are obtained when the Lys(iPr) substitution is made at both the six and eight positions (compare compound (4) to compound 10)).

When an Ile substitution is made in addition to the Lys(iPr)$^{6,8}$ substitutions, potent antiovulatory activity is retained and histamine release activity is lowered beyond that of the Lys(iPr)$^{6,8}$ substitutions alone (compare compound (4) to (7)).

In the design of LHRH antagonist analogs having high antiovulatory potency general considerations governing the selection of substitutions for the residues of positions 1-4, 7, 9 and 10 are known in the art as described, for example, in U.S. Pat. No. 4,481,190 to Nestor. In addition, the N-terminus of the analog shuld be designed so as to be hydrophobic.

Compounds (3) through (12) of Table I are examples of analogs of the persent invention.

Synthesis Of Analogs

All of the analogs listed in Table I were synthesized by the solid phase method using a Beckman automated synthesizer. The support was 1.43 g of a methylbenzhydrylamine (MBHA) resin having 0.35 meq amino group per gram, giving a theoretical yield of 0.5 millimole. Briefly, a 2.5-fold excess of each Boc amino acid and of hydroxybenzotriazole is used, coupling for two hours in a 1:1 mixture of DMF and dichloromethane. Alpha methyl residues require at least twelve hours for complete coupling. The Boc protecting group is removed by a thirty-minute treatment with 50% trifluoroacetic acid in $CHCl_3$, preceded by a five minute pretreatment with the same reagent. Liquid HF, $O^0$, 45 min., is used to cleave the peptide from the resin, and the peptide is extracted into aq. acetic acid and lyophilized. The crude product, usually about 500 mg, is purified by high performance chromatography on $C_{18}$ silica gel, eluting with a mixture of acetonitrile and 0.1% TFA in water. Fractions that are homogeneous by tlc and UV absorption are combined and lyophilized. A Waters analytical HPLC is used to determine percent purity of the final product. All of the peptides have been at least 98% pure.

Antiovulatory Activity Assay

Antiovulatory activity was determined by standard antiovulatory assays conducted by the method described by Corbin and Beattie, Endocrine Research Communications 2 1 (1975) and results are given in Table I.

Histamine Releasing Activity Assay

The in vitro histamine release activity of the analogs was assayed by the method described below and the results are given in Table I.

A suspension of rat mast cells was added to increasing concentrations of peptide and the mixture was incubated for a few minutes followed by centrifugation to collect the histamine in the supernatant. A PIPES (piperazine-N,N'-bis[2-ethanesulfonic acid]) medium buffered at pH 7.4 containing NaCl 119 mM, KCl 5 mM, PIPES 25mM, NaOH 40 mM, glucose 5.6 mM, $CaCl_2$ 1 mM and 0.1% bovine serum albumin was used. This was designated as PIPES AC. Peptides were dissolved in double distilled $H_2O$ at a concentration of 2 mg ml and stored at $-20°$ C. They were thawed just prior to testing, duluted in PIPES AC and prewarmed for 5 min. at 37° C. Peptides studied were stable to heating at 56° C. for 2 hr., and to freezing and thawing.

Peritoneal cells were collected from male Sprague-Dawley rats weighing 200 to 250 gm and purchased from Harlan (Madison, Wis.). After euthanasia by $CO_2$, the peritoneal cavity was washed with 50 ml PIPES AC medium containing 20 units of heparin. Following centrifugation at $200 \times g$ for 8 min. at 4° C., cells were washed again and finally resuspended to a concentration of 8 to $24 \times 10^5$ total leukocytes/ml in PIPES AC. This suspension contained approximately 5-10% mast cells. Washed cells were used immediately after collection and were prewarmed for 5 min. at 37° C. prior to pipetting 0.25 ml aliquots into $12 \times 75$ mm polystyrene tubes containing 0.25 ml of diluted peptide. Mixtures were incubated for 15 min at 37° C. and the reaction stopped by centrifugation at $400 \times g$ for 15 min at 4° C. The cell supernatants were assayed for histamine content by the automated fluorometric assay procedure as described by Siraganian in "An Automated Continuous Flow System For The Extraction And Fluorometric Analysis Of Histamine", Anal. Biochem., 57 383 (1974), and by Siraganian and Hook in "Histamine Release And Assay Methods For The Study of Human Allergy" in "Manual of Clinical Immunology" 3rd ed., N. R. Rose, H. Friedman, and J. L. Fahey (Eds.) Amer. Soc. for Microbiology, Washington, 1986, p. 808. Alternatively, the more laborious manual fluorometric assay method may be employed which gives similar results as described by Siraganian and Hook. The LHRH analog [N-Ac-D-Nal(2)$^1$ D-pCl-Phe$^2$, D-Trp$^3$, D-Arg$^6$, D-Ala$^{10}$] LHRH (compound (1) of Table I) was tested with the mast cells of each rat as a standard in each experiment.

Characteristics of The Histamine Release Reaction

The $ED_{50}$ values of Table I (mean effective dose from dose response curves), are expressed in $\mu$g/ml. The most potent histamine releasing compounds are the LHRH antagonists such as compound (1), while LHRH antagonist analogs of the present invention were markedly less potent as histamine releasers. Dose response curves are typically steep across the 50% endpoint; the peptides usually achieved 100% histamine release at higher concentrations. Typically, in generating dose response curves to obtain $ED_{50}$ values mast cells were purified to greater than 90% by centrifugation through Percoll and incubated for 15 min with the histamine releasing compound. The response curves and $ED_{50}$ values were similar to those obtained with unpurified cell suspensions, suggesting that other cell types are not required for histamine release. For routine testing, mast cells were not purified. In other experiments, where mast cell supernatants were concomitantly assayed for release of lactic dehydrogenase, there was no evidence seen of cell toxicity induced by LHRH or any analog tested. There was no enhancement of histamine release by phosphatidyl serine with LHRH and the analogs listed in Table I. This is in contrast to the IgE-triggered release reaction from rat mast cells which is highly dependent on the addition of phosphatidyl serine to reaction mixtures.

Other differences from allergic-type release include the short incubation time required and the lack of a calcium requirement. The time needed for maximal histamine release was less than 1 min, even at less than optimal peptide concentrations. Neither added calcium nor magnesium ions were essential for histamine release by LHRH, or the analogs tested. However, with these agents, greater release occurred when 1 mM Ca++ was included in the medium. Less release was seen when 1 mM Mg++ was substituted for 1 mM Ca++. Histamine release was greater at 25° C. and 27° C. than at 17° C., and no release occurred when cells were incubated with peptide at 1° C. This is further suggestive evidence that the histamine release is due to a secretory rather than cytolytic effect of the peptides.

Method of Use

Treatment of subjects with these analogs is generally carried out in the same manner as the clinical treatment using other LHRH antagonists as described in U.S. Pat. No. 4,547,370 to Roeske. Pharmaceutically acceptable salts of these analogs are the corresponding salts of known analogs as described in U.S. Pat. No. 4,547,370 to Roeske.

While the foregoing describes and gives examples of novel LHRH antagonist analogs having low histamine releasing activity and methods for controlling the release of gonadatropic hormones in mammals, these examples are not intended nor should they be construed as limitations on the invention. As one skilled in the art would understand, many variations and modifications may be made in the specific examples provided herein that fall within the spirit and scope of this invention.

TABLE I

| HISTAMINE RELEASING POTENCY AND ANTIOVULATORY POTENCY OF LHRH ANALOGS | | |
|---|---|---|
| Analog | In Vitro Histamine Release (ug/ml) $ED^{50}$ | Ovulation Inhibition (ug/rat) Corn Oil $ED^{100}$ |
| 1. [N—Ac—D-Nal(2)$^1$D-pCl—Phe$^2$,D-Trp$^3$,D-Arg$^6$,D-Ala$^{10}$]LHRH | 0.10 | 1.0 |
| 2. [N—Ac—D-Nal(2)$^1$,D-C—α-Me—pCl—Phe$^2$,D-Pal(3)$^3$,D-Arg$^6$,hArg(Et$_2$)$^8$,D-Ala$^{10}$]LHRH | 4.9 | 1.0 |
| 3. [N—Ac—D-Nal(2)$^1$,D-C—α-Me—pCl—Phe$^2$,D-Pal(3)$^3$,D-Arg$^6$,Lys(iPr)$^8$,D-Ala$^{10}$]LHRH | 4.0 | 1.0 |
| 4. [N—Ac—D-Nal(2)$^1$,D-pCl—Phe$^2$,D-Trp$^3$,D-Lys(iPr)$^6$,Lys(iPr)$^8$,D-Ala$^{10}$]LHRH | 6.6 | 1.0 |
| 5. [N—Ac—D-Nal(2)$^1$,D-C—α-Me—pCl—Phe$^2$,D-Pal(3)$^3$,Lys(iPr)$^5$,D-Tyr$^6$,Lys(iPr)$^8$,D-Ala$^{10}$]LHRH | 3.2 | 1.0 |
| 6. [N—Ac—D-Nal(2)$^1$,D-pCl—Phe$^2$,D-Pal(3)$^3$,Lys(iPr)$^5$,D-Tyr$^6$,D-Ala$^{10}$]LHRH | 1.97 | 1.0 |
| 7. [N—Ac—D-Nal(2)$^1$,D-pCl—Phe$^2$,D-Pal(3)$^3$,Ile$^5$,D-Lys(iPr)$^6$,Lys(iPr)$^8$,D-Ala$^{10}$]LHRH | 9.92 | ≧0.5 |
| 8. [N—Ac—D-Nal(2)$^2$,D-pCl—Phe$^2$,D-Pal(3)$^3$,D-MePal$^5$,Lys(iPr)$^8$,D-Ala$^{10}$]LHRH | 7.1 | |
| 9. [N—Ac—D-Nal(2)$^1$,D-pCl—Phe$^2$,D-Pal(3)$^3$,MePal$^5$,D-Tyr$^6$,Lys(Me$_3$)$^8$,D-Ala$^{10}$]LHRH | 5.62 | |
| 10. [N—Ac—D-Nal(2)$^1$,D-pCl—Phe$^2$,D-Pal(3)$^3$,MePal$^5$,D-Tyr$^6$,Lys(iPr)$^8$,D-Ala$^{10}$]LHRH | 4.33 | ≧0.5 |
| 11. [N—Ac—D-Nal(2)$^1$,D-pCl—Phe$^2$,D-Pal(3)$^3$,Lys(iPr)$^5$,D-MePal$^6$,Lys(iPr)$^8$,D-Ala$^{10}$]LHRH | 9.72 | ≧ ≧0.5 |
| 12. [N—Ac—D-Nal(2)$^1$,D-pCl—Phe$^2$,D-Pal(3)$^3$,MePal$^5$,D-Lys(iPr)$^6$,Lys(iPr)$^8$,D-Ala$^{10}$]LHRH | 7.9 | ≧ ≧0.5 |

Histamine release determinations were performed in duplicate or triplicate using mast cells from a minimum of three individual rats.
The symbol (≧) denotes the facts that there was a statistically significant reduction in the rats ovulating compared to the control although an ED$_{100}$ value was not achieved at the dose indicated.
The symbols (≧ ≧) indicate that, at the dose tested, the analog was inactive.

I claim:

1. A compound of the formula

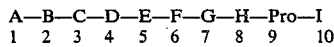

A—B—C—D—E—F—G—H—Pro—I
1  2  3  4  5  6  7  8  9  10 and the pharmaceutically acceptable salts thereof wherein:

A: is an amino acyl residue selected from the group consisting of N-Ac-D,L-phenylalanyl, N-Ac-D,L-p-chlorophenylalanyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, and 3-(4-trifluoromethylphenyl)-D,L-alanyl;

B: is an amino acyl residue selected from the group consisting of D-phenylalanyl, D-p-Cl -phenylalanyl, D-p-F-phenylalanyl, 3-(3,4,5-trimethoxyphenyl)-D-alanyl, D-α-methyl-p-Cl-phenylalanyl and 3-(2,4,6-trimethylphenyl)-D-alanyl;

C: is an amino acyl residue selected from the group consisting of D-tryptophanyl, D-phenylalanyl, D-Me$^5$phenylalanyl, 3-(3-pyridyl)-D-alanyl, 3-(1-naphthyl)-D-alanyl, and 3-(2-naphthyl)-D-alanyl;

D: is an amino acyl residue selected from the group consisting of L-seryl and L-ornithyl;

E: is an amino acyl residue selected from the group consisting of tyrosyl, Nε-isopropyl lysyl, isoleucyl, arginyl, lysyl and N-methyl 3-pyridinium alanyl;

F: is an amino acyl residue selected from the group consisting of D-arginyl, D-Nε-isopropyl lysyl, D-tyrosyl, D-N-methyl 3 pyridinium alanyl, D-tryptophanyl, and 3-2-naphthyl-D-alanyl;

G: is an amino acyl residue selected from the group consisting of leucyl, norleucyl, norvalyl and phenylalanyl;

H: is the amino acyl residue Nε-isopropyl lysye:

I: is a member selected from the group consisting of D-alaninamide, D-leucinamide, glycinamide; and —NHR wherein R is alkyl having from one to four carbon atoms, or NHCONH$_2$.

2. The compound of claim 1 wherein E is tyrosyl, F is D-arginyl.

3. The compound of claim 1 wherein E is tyrosyl, F is D-Nε-isopropyl lysyl.

4. The compound of claim 1 wherein E is Nε-isopropyl lysyl, F is D-tyrosyl.

5. The compound of claim 1 wherein E is isoleucine, wherein F is D-Nε-isopropyl lysyl.

6. The compound of claim 1 wherein E is tyrosyl, F is D-N-methyl-3-pyridinium alanyl.

7. The compound of claim 1 wherein E is N-methyl-3-pyridinium alanyl, F is D-tyrosyl.

8. The compound of claim 1 wherein E is Nε-isopropyl lysyl, F is D-N-methyl-3-pyridinium alanyl.

9. The compound of claim 1 wherein E is N-methyl-3-pyridinium alanyl, F is D-Nε-isopropyl lysyl.

10. A compound of the formula: [N-Ac-D-Nal(2)$^1$, D-C-α-Me-pCl-Phe$^2$, D-Pal(3)$^3$, D-Arg$^6$, Lys(iPr)$^8$, D-Ala$^{10}$]LHRH.

11. A compound of the formula: [N-Ac-D-Nal(2)$^1$, D-pCl -Phe$^2$, D-Trp$^3$, D-Lys(iPr)$^6$, Lys(iPr)$^8$, D-Ala$^{10}$]LHRH.

12. A compound of the formula: [N-Ac-D-Nal(2)$^1$, D-C-α-Me-pCl -Phe$^2$, D-Pal(3)$^3$, Lys(iPr)$^5$, D-Tyr$^6$, Lys(iPr)$^8$, D-Ala$^{10}$]LHRH.

13. A compound of the formula: [N-Ac-D-Nal(2)$^1$, D-pCl -Phe$^2$, D-Pal(3)$^3$, Ile$^5$, D-Lys(iPr)$^6$, Lys(iPr$^8$), D-Ala$^{10}$]LHRH.

14. A compound of the formula: [N-Ac-D-Nal(2)$^1$, D-pCl -Phe$^2$, D-Pal(3)$^3$, D-MePal$^6$, Lys(iPr)$^8$, D-Ala$^{10}$]LHRH.

15. A compound of the formula: [N-Ac-D-Nal(2)$^1$, D-pCl -Phe$^2$, D-Pal(3)$^3$, MePal$^5$, D-Trp$^6$, Lys(iPr)$^8$D-Ala$^{10}$]LHRH.

16. A compound of the formula: [N-Ac-D-Nal(2)¹, D-pCl-Phe², D-Pal(3)³, Lys(iPr)⁵, D-MePal⁶, Lys(iPr)⁸, D-Ala¹⁰]LHRH.

17. A compound of the formula: [N-Ac-D-Nal(2)¹, D-pCl-Phe², D-Pal(3)³, MePal⁵, D-Lys(iPr)⁶, Lys(iPr)⁸, D-Ala¹⁰]LHRH.

18. A method for regulating the release of gonadatropic hormones by the pituitary gland of mammals comprising:

administering an effective amount of peptide or pharmaceutically
acceptable salt thereof, said peptide having the formula:

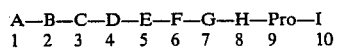

A—B—C—D—E—F—G—H—Pro—I
1　2　3　4　5　6　7　8　9　10 wherein:
A: is an amino acyl residue selected from the group consisting of N-Ac-D,L-phenylalanyl, N-Ac-D,L-p-chlorophenylalanyl, N-Ac-D,L-alanyl, 3-(1-naphthyl)-D,L-alanyl, 3-(2-naphthyl)-D,L-alanyl, 3-(2,4,6-trimethylphenyl)-D,L-alanyl, and 3-(4-trifluoromethylphenyl)-D,L-alanyl;

B: is an amino acyl residue selected from the group consisting of D-phenylalanyl, D-p-Cl-phenylalanyl, D-p-F-phenylalanyl, 3-(3,4,5-trimethoxyphenyl)-D-alanyl, D-α-methyl-p-Cl-phenylalanyl and 3-(2,4,6-trimethylphenyl)-D-alanyl;

C: is an amino acyl residue selcted from the group consisting of D-tryptophanyl, D-phenylalanyl, D-Me⁵phenylalanyl. 3-(3-pyridyl)-D-alanyl, 3-(1-naphthyl)-D-alanyl, and 3-(2-naphthyl)-D-alanyl;

D: is an amino acyl residue selected from the group consisting of L-seryl and L-ornithyl;

E: is an amino acyl residue selected from the group consisting of tyrosyl, Nε-isopropyl lysyl, isoleucyl, arginyl, lysyl and N-methyl 3-pyridinium alanyl;

F: is an amino acyl residue selected from the group consisting of D-arginyl, D-Nε-isopropyl lysyl, D-tyrosyl, D-N-methyl 3 pyridinium alanyl, D-tryptophanyl, and 3-2-naphthyl-D-alanyl;

G: is an amino acyl residue selected from the group consisting of leucyl, norleucyl, norvalyl and phenylalanyl;

H: is the amino acyl residue Nε-isopropyl lysine;

I: is a member selected from the group consisting of D-alaninamide, D-leucinamide, glycinamide; and —NHR wherein R is alkyl having from one to four carbon atoms, or NHCONH₂.

19. A method for regulating the release of gonadatropic hormones by the pituitary gland of mammals comprising:

administering an effective amount of peptide of pharmaceutically accepted salt thereof, said peptide selected from the group consisting of: [N-Ac-D-Nal(2)¹, D-pCl-Phe², D-Pal(3)³, Ile⁵, D-Lys(iPr)⁶, Lys(iPr⁸, D-Ala¹⁰]LHRH, [N-Ac-D-Nal(2)¹, D-pCl-Phe², D-Pal(3)³, Lys(iPr)⁵, D-MePal⁶, Lys(iPr)⁸, D-Ala¹⁰]LHRH, [N-Ac-D-Nal(2)¹, D-pCl-Phe², D-Pal(3)³, MePal⁵, D-Lys(iPr)⁶, Lys(iPr)⁸, D-Ala¹⁰]LHRH, [N-Ac-D-Nal(2)¹, D-pCl-Phe², D-Pal(3)³, D-MePal⁶, D-Lys(iPr)⁶, D-Ala¹⁰]LHRH, [N-Ac-D-Nal(2)¹, D-pCl-Phe², D-Trp³, D-Lys(iPr)⁶, Lys(iPr)⁸, D-Ala¹⁰]LHRH [, and [N-Ac-D-Nal(2)¹, D-pCl-Phe², D-Pal(3)³, MePal⁵, D-Tyr⁶, Lys(Me₃)⁸, D-Ala¹⁰]LHRH].

* * * * *